United States Patent [19]

Shimizu et al.

[11] Patent Number: 4,731,483
[45] Date of Patent: Mar. 15, 1988

[54] METHOD FOR PREPARING 3-ETHYLBENZOPHENONE

[75] Inventors: Isoo Shimizu; Yasuo Matsumura, both of Yokohama; Shigenobu Kawakami, Ichikawa; Atsushi Sato, Tokyo, all of Japan

[73] Assignee: Nippon Petrochemicals Co., Ltd., Tokyo, Japan

[21] Appl. No.: 904,470

[22] Filed: Sep. 8, 1986

[30] Foreign Application Priority Data

Sep. 11, 1985 [JP] Japan ................. 60-200808

[51] Int. Cl.$^4$ .......................................... C07C 45/36
[52] U.S. Cl. ................................. 568/311; 568/321; 585/459
[58] Field of Search .................... 568/321; 585/459

[56] References Cited

U.S. PATENT DOCUMENTS 3,899,537  8/1975  Holtz ...................... 568/321
3,965,185  6/1976  Young .................... 568/321
4,299,987 11/1981  Dalhyj et al. ........... 568/321

Primary Examiner—James H. Reamer
Attorney, Agent, or Firm—Fisher, Christen & Sabol

[57] ABSTRACT

The present invention provides a method for preparing 3-ethylbenzophenone in a high purity which comprises the steps of alkylating benzene with ethylene with the aid of an alkylating catalyst to obtain an alkylated product composed mainly of unreacted benzene, ethylbenzene, polyethylbenzenes and heavier by-products; subjecting the alkylated product to distillation in order to recover therefrom a fraction which has a temperature range of boiling points within the range of 275° to 310° C. (in terms of atmospheric pressure); dehydrogenating the recovered fraction at a reaction temperature within the range of 200° to 700° C. in the presence of a dehydrogenating catalyst; oxidizing the dehydrogenated fraction in a liquid phase; and performing distillation to recover therefrom 3-ethylbenzophenone represented by the formula:

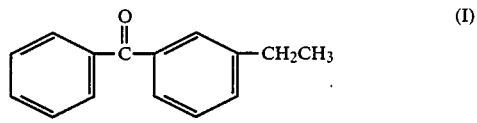

11 Claims, No Drawings

METHOD FOR PREPARING 3-ETHYLBENZOPHENONE

BACKGROUND OF THE INVENTION (i) Field of the Invention

The present invention relates to a method for preparing 3-ethylbenzophenone represented by the formula (I) which is important as a material for the synthesis of medicines, Ketoprofen (trade name):

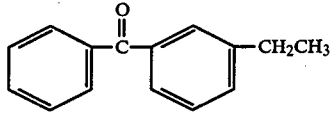

(ii) Description of the Prior Art

As a method for preparing 3-ethylbenzophenone, there is known, for example, a method in which a Friedel-Crafts alkylation is carried out by the use of benzophenone and diethyl sulfate in the presence of aluminum chloride in order to obtain the desired 3-ethylbenzophenone (Spanish Pat. No. 452500). In this Spanish patent, it is also disclosed that a ketoprofen which is a kind of medicine is synthesized from this 3-ethylbenzophenone. However, this method of Spanish patent results in the formation of various by-products, though high-purity raw materials are employed therein. Consequently, in the Spanish patent, the purification of the desired product is difficult and its yield is low.

SUMMARY OF THE INVENTION

An object of the present invention is to provide a method for synthesizing high-purity 3-ethylbenzophenone from specific materials at a low cost.

In the present invention, benzene is first alkylated with ethylene with the aid of an alkylating catalyst in order to prepare an alkylated product composed mainly of unreacted benzene, ethylbenzene, polyethylbenzenes and heavier by-products. Then, distillation is carried out to recover a fraction which has a temperature range of boiling points of 275° to 310° C. (in terms of atmospheric pressure) from the alkylated product. The recovered fraction is afterward dehydrogenated at a temperature within the range of 200° to 700° C. in the presence of a dehydrogenating catalyst, and after oxidization in a liquid phase, a distilling operation is then performed in order to prepare high-purity 3-ethylbenzophenone (hereinafter referred to simply as EBP).

The starting material of the present invention is a by-produced oil, that is, a mixture of various compounds chemical structures of which are not known, and thus it has not been employed yet as a material for a chemical reaction.

DESCRIPTION OF THE PREFERRED EMBODIMENTS

For the purpose of preparing a styrene monomer for a polystyrene by dehydrogenation of ethylbenzene, it has been extensively carried out on an industrial scale that benzene is alkylated with ethylene to form ethylbenzene.

In the preparation of ethylbenzene, benzene is first alkylated with ethylene in the presence of an alkylating catalyst in order to prepare an alkylated product mainly comprising unreacted benzene, ethylbenzene, polyethylbenzenes and heavier substances containing the EPEA. In this case, a known method for preparing ethylbenzene such as a liquid phase alkylation method or a gaseous phase alkylation method may be utilized. A practical molar ratio of benzene to ethylene can be within the range of about 25:1 to 2:1, preferably about 10:1 to 3:1. In the liquid phase reaction, usable examples of the alkylating catalysts include Friedel-Crafts catalysts such as aluminum chloride, aluminum bromide and organic aluminum halides; Lewis acids such as $ZnCl_2$, $FeCl_3$ and $BF_3$ to which a promotor is added; and Brönsted acids such as sulfuric acid, sulfonic acid and p-toluene-sulfonic acid. The above mentioned alkylating catalyst may be employed in an amount of about 0.002 to 0.050 part by weight, preferably about 0.005 to 0.030 part by weight based on the weight of the produced ethylbenzene, and benzene may be reacted with ethylene within the temperature range of about 0° to 175° C., preferably about 20° to 150° C. When the reaction temperature is less than 0° C., the yield of ethylbenzene will deteriorate, and when it is more than 175° C., the yield of ethylbenzene will also drop inconveniently owing to side reactions. With regard to a reaction pressure, a high pressure is preferable because of facilitating the dissolution of ethylene, but the pressures up to 100 $kg/cm^2$ are applicable and practicable. A suitable reaction time is usually within the range of about 10 minutes to 10 hours, preferably about 20 minutes to 3 hours.

In the gaseous phase alkylation method, for example, the reactants may be caused to stream over a suitable alkylating catalyst in which phosphoric acid is incorporated into diatomaceous earth, silica, alumina or aluminum silicate, at a temperature within the range of about 250° to 450° C., preferably about 300° to 400° C. at a pressure within the range of about 28 to 85 $kg/cm^2$, preferably about 42 to 70 $kg/cm^2$ at an ordinary space rate.

As a result of such a reaction, there is prepared an alkylated product mainly consisting of unreacted benzene, the desired ethylbenzene, polyethylbenzenes and heavier substances. If necessary, the alkylating catalyst mixedly present in the alkylated product may be removed therefrom. When, e.g., aluminum chloride is used as the alkylating catalyst, the alkylated product may be delivered to a settling tank, in which the used aluminum chloride catalyst may be precipitated and removed therefrom. If necessary, the removed catalyst may be recycled through and reused in the reaction system. On the other hand, the remaining alkylated product is washed with water and then neutralized.

Next, distillation is carried out to recover a starting material fraction of the present invention which has a temperature range of boiling points of 275° to 310° C. (in terms of atmospheric pressure), from the alkylated product mainly consisting of unreacted benzene, ethylbenzene, polyethylbenzenes and heavier substances.

In this recovery process, the alkylated product is distilled under a normal to reduced pressure to distill away unreacted benzene (boiling point 80° C.), ethylbenzene (boiling point 136° C.) and polyethylbenzenes (boiling points 176° to 250° C.) and to thereby obtain the heavier substances, and the latter is further distilled, whereby the starting material fraction of the present invention can be procured. Alternatively, the direct distillation of the alkylated product is also possible, and it permits preparing the desired starting material fraction of the present invention. Either recovery process can be selected.

The distillation can be preferably carried out under a reduced pressure of 100 mmHg or less by the use of one or plural towers in each of which the number of theoretical separation plates is 5 or more, preferably 10 or more.

According to such a distillation, there can be recovered, as the material fraction of the present invention, the fraction which has a temperature range of boiling points of 275° to 310° C. (in terms of atmospheric pressure) from the above mentioned alkylated product. When the fraction having a boiling point of more than 310° C. is used, the EBP which is the desired object will be poor in purity and its yield will also deteriorate unpreferably. In consequence, it is important to take care so that the starting material fraction of the present invention may not substantially contain the components having the boiling points more than 310° C. Inversely, when the components having the boiling points of less than 275° C. are contained therein, the yield of the EBP which is the object of the present invention will go down disadvantageously.

The material fraction of the present invention contains 1,1-(3-ethylphenyl)phenylethane (hereinafter referred to as EPEA) a boiling point of which is not known yet. Even if the boiling point of the material fraction is found and known, the latter will be naturally different from a multi-component system in a fractional temperature in the distillation. It has been confirmed by the inventors of the present application that 1,1-(2-ethylphenyl)phenylethane which is an ortho-isomer of the EPEA is extremely close to the EPEA in the boiling point, and thus its separation from the EPEA by the rectification is absolutely impossible. For this reason, the incorporation of the orth-isomer into the material must be avoided to the utmost, but the present invention is advantageous and convenient, because the starting material fraction of the present invention contains substantially no orth-isomer. Further, it has also been confirmed that 1,1-(4-ethylphenyl)phenylethane which is the para-isomer of the EPEA has a boiling point in the vicinity of that of the EPEA.

Therefore, it is possible that an operation is made so as to prevent the material fraction of the present invention from containing the para-isomer, though being difficult. However, even if such a fraction in a boiling range as contains the para-isomer is used as the starting fraction of the invention, the desired EBP can be obtained in a high purity according to the method of the present invention. In consequence, the para-isomer which is hard to treat as described above may be contained in the material fraction of the present invention. This is an advantageous point of the present invention.

Moreover, the starting material fraction of the present invention contains, in addition to the EPEA, many complicated hydrocarbon compounds such as polyalkylbenzenes the boiling points of which are extremely near to that of the EPEA. With regard to these compounds, it is difficult to elucidate their correct chemical structures, and their kinds and compositions are not constant in the starting material fraction, since they are by-products. It should also be noted that these compounds are absolutely difficult to separate therefrom. The reason why the aforesaid material fraction has not been utilized as a raw material of a chemical reaction is that the fraction is composed of extremely numerous kinds of compounds.

Next, the material fraction of the present invention is dehydrogenated at a reaction temperature of 200° to 700° C. in the presence of a dehyrogenating catalyst. This dehydrogenation permits preparing olefins such as 1,1-(3-ethylphenyl)phenylethylene (hereinafter referred to as EPEL for convenience) and the like. The EPEL which can be prepared herein is a novel compound referred to at the end of a literature.

The dehydrogenating reaction of the present invention can be accomplished by a known liquid phase reaction or gaseous phase reaction, but in general, the latter is more preferable on account of its brevity.

As the dehydrogenating catalyst, any one can be employed, in so far as it can dehydrogenate an aromatic alkyl into an aromatic alkene, and examples of the dehydrogenating catalysts include simple substances such as iron, platinum, palladium, molybdenum, vanadium, aluminum, nickel, chromium, zinc, tungsten, copper, cerium, thorium, lanthanum, neodymium, yttrium, thulium, erbium and praseodymium; oxides thereof; and mixtures thereof. Preferable dehydrogenating catalysts are iron oxide series and chromia-alumina series catalysts.

A reaction temperature for the dehydrogenation can be selected optionally within the range of 200° to 700° C. in compliance with the used catalyst and reactive phase, and for examples, in the case of the gaseous reaction, the reaction may be carried out within the temperature range of 300° to 700° C., preferably 350° to 500° C. When the reaction temperature of the dehydogenation is lower than 200° C., a dehydrogenation rate will fall and the yield of the object aimed by the present invention will drop; when it is higher than 700° C., by-products will be increased and the yield will also drop disadvantageously. A feed rate (SV) of the materials may be from 0.5 to 10 hr$^{-1}$ or so. Further, a reaction pressure is generally from a reduced pressure to 3 kg/cm$^2$ or so.

In the case of the dehydrogenation in the gaseous phase, the materials are preferably diluted with an inert gas such as steam, nitrogen, a carbonic acid gas, a rare gas, or a lower hydrocarbon such as methane, ethane or propane for the prevention of coking and for the drop in the partial pressure of the material fraction with the intention of improving the yield. The particularly preferable gas for the dilution is steam.

After the dehydrogenation, cooling and, if desired, the separation of the diluting gas are carried out. Afterward, the fraction containing the EPEL is subjected to oxidation in the following process.

For the subsequent oxidation process, it is not necessary at all to isolate the EPEL itself, e.g., by extraction (even by any distillation, the isolation cannot be achieved) after the dehydrogenation. Therefore, the unreacted components which have not been dehydrogenated, and the olefins other than the EPEL will be directly subjected, as a mixture thereof, to the following oxidation process. Even in the case of such a mixture, the method of the present invention permits obtaining the EBP in a high purity preferably. When needed, however, more volatile components produced by decomposition reactions involved in the dehydrogenation process and heavier components formed by thermal polymerization reactions in the same process can be separated therefrom by the distillation.

The liquid oxidation methods of the present invention include an oxidation with molecular oxygen in the presence or the absence of the metallic oxidizing catalyst and another oxidation by the use of an oxidizing agent such as a permanganate, a chromate, lead tetracetate, a periodate, ruthenium tetroxide, osmium tetroxide, hydrogen peroxide, ozone and a mixture thereof.

The oxidation with molecular oxygen is extremely easy, and it can be accomplished without any catalyst but a reaction rate of the oxidation can be heightened, if the catalyst is employed.

Examples of the catalysts used in the oxidation with the aid of molecular oxygen include salts of metals in the groups VI-b, VII-b and VIII of the periodic table such as chromium, manganese, tungsten, molybdenum, platinum, palladium, cobalt, nickel, iron, rhodium and ruthenium, and mixtures thereof. In particular, the salts of cobalt, iron, manganese and chromium are preferred. As the forms of the salts, naphthenates are preferable. A proper amount of the used catalyst is, for example, within the range of 0.05 to 10% by weight based on the weight of the starting material fraction. The above mentioned molecular oxygen may be fed to the reaction system in the form of pure oxygen, air or a mixture of pure oxygen and another inert gas.

A reaction temperature of the oxidation by the molecular oxygen is from 30° to 250° C., preferably from 50° to 200° C. When the reaction temperature is less than 30° C., a reaction rate will be remarkably low; when it is more than 250° C., a selectivity of the desired EBP will be noticeably low, and after all, both the above cases are not preferable.

A pressure condition in the oxidation with the molecular oxygen is not particularly limited and can be selected within the range of atmospheric pressure to 50 kg/cm$^2$.

Additionally, an inert solvent can also be used, but usually without any inert solvent, the intended oxidation can be achieved by feeding the molecular oxygen to the material oil.

In the oxidation with the aid of the above mentioned oxidizing agents such as permanganate, however, it is preferred to make use of the inert solvent for the purpose of improving its contact efficiency with the oxidizing agent. Examples of such inert solvents include water, acetone, alcohols such as t-butyl alcohol and the like, glacial acetic acid, acetic acid, isooctane, benzene, chloroform and pyridine, and mixtures thereof.

Concrete examples of the above mentioned oxidizing agents include potassium permanganate, chromium trioxide, sodium dichromate, sodium periodate, potassium periodate, lead tetracetate, ruthenium tetracetate, osmium tetracetate, hydrogen peroxide and ozone, and mixtures thereof. The preferable oxidizing agents are permanganates, chromates and ozone.

With regard to an amount of the oxidizing agent such as a permanganate, at least 1 equivalent, preferably 1.5 equivalents or more based on the material fraction are necessary. An upper limit of its amount is not particularly limited, but usually, the amount of more than 10 equivalents is merely uneconomical and thus unpreferable. A reaction temperature of the oxidation with the oxidizing agent is within the range of 0° to 200° C., preferably 30° to 150° C. When the reaction temperature is less than 0° C., the reaction will not make progress; when it is more than 200° C., by-products will be formed, which fact will result in the remarkable deterioration in the yield of the EBP disadvantageously.

Olefins such as the EPEL undergo an oxidative cleavage at a carbon-carbon double bond or bonds contained in the olefins by the oxidation of the present invention.

After the oxidation, if necessary, the used oxidizing agent, the oxidizing solvent and the oxidizing catalyst are separated out by means of filtration or the like, alternatively the reaction mixture is extracted with an organic solvent such as benzene, ethyl acetate or chloroform to remove the solvent used in the dehydrogenation or oxidation, and a usual distillation is then carried out to recover the high-purity EBP.

In this distillation process, if the EBP is recovered as the fraction within the boiling range of 310° C. and not more than 340° C. (in terms of atmospheric pressure), preferably 320° to 333° C., the high-purity EBP can be prepared.

Further, even if the para-isomer of the EPEA is contained in the starting material fraction of the present invention, dehydrogenated substances derived therefrom and their oxides can easily be separated by the distillation operation of recovering the fraction containing the aforesaid EBP, and as a result thereof, the high-purity EPB can be obtained.

As described above in detail, the material fraction of the present invention is the specific fraction produced from the alkylation of benzene with ethylene, and thus the desired EBP can be prepared at a very low cost. Further, since the fraction prepared by the specific manufacturing method is used as the starting material, there can be obtained the high-purity EBP containing no orth- and para-isomers.

Since the starting material fraction of the present invention contains many hydrocarbons chemical structures of which are not known, it cannot be presumed how these components behave in certain reactions. In addition, these components having unknown structures cannot be separated in fact even by the technique of rectification.

However, in view of the fact that the dehydrogenation and the subsequent oxidative reaction of the present invention permit preparing the high-purity EBP, it can be supposed that the structurally unknown components in the starting material fraction scarcely take part in the reactions or are converted into other compounds which will be separated out by the subsequent distillation. Therefore, according to the present invention, the high-purity EBP can be obtained from the specific fraction containing many components the chemical structures of which are known and which cannot be separated out by the distillation.

Now, the present invention will be described in detail in reference to examples, but the latter do not intend to limit the scope of the present invention.

EXAMPLES

Experiment 1

In a reactor equipped with a stirrer, benzene was brought into contact with ethylene in a molar ratio of benzene:ethylene being 9:1 in the presence of aluminum chloride at a temperature of 130° C. at a pressure of 4.9 kg/cm$^2$ for 1 hour in a liquid phase in order to convert all of ethylene. An amount of used aluminum chloride was 0.0034 part by weight based on ethylbenzene produced. Aluminum chloride was then removed from the resultant alkylated product, and analysis was carried out by means of GC. It was found from the analytical results that there existed therein 49.0% by weight of benzene, 32.9% by weight of ethylbenzene, 17.5% by weight of polyethylbenzenes and 0.5% by weight of heavier substances. The alkylated product was then distilled to recover benzene, ethylbenzene and polyethylbenzenes, so that heavier substances were obtained in an amount of 0.014 part by weight based on ethylbenzene produced. These heavier substances were further subjected to distillation in order to procure a fraction having a boiling point of 280° to 310° C. (in terms of atmospheric pressure), and the procured fraction was then analyzed by means of GC. It was found from the analytical results that the fraction was composed of 76% by weight of the EPEA, 6% by weight of p-isomer of the EPEA and the remainder consisting of polyalkylbenzenes and various other hydrocarbons.

The above mentioned distillation was carried out at a reduced pressure of 5 mmHg, the number of theoretical separation plates being 15.

From the above mentioned material fraction, the EPEA itself could be analyzed anyway in accordance with the GC analysis using capillary columns. The EPEA alone could not be separated from the other components present in the above mentioned material fraction even by the rectification, since the other components have boiling points close to or equal to that of the EPEA.

An iron oxide series dehydrogenating catalyst (trade name 64C; Nissan Girdler Co., Ltd.) containing chromium oxide and alumina was prepared so as to have a grain diameter of 0.5 to 1 mm, and a stainless pipe having an inner diameter of 10 mm and a length of 60 cm was then filled with the thus prepared dehydrogenating catalyst. The above mentioned fraction was caused to pass through the catalytic layer at 40 ml/hr together with water at 40 m/hr at a temperature of 400° C. under atmospheric pressure via a preheating pipe in order to accomplish dehydrogenation therein. The reaction product was then cooled to room temperature, followed by a gas-liquid separation. The resultant organic layer was afterward subjected to the GC analysis with the intention of making sure of reactivity and selectivity. The analytical results indicated that the reaction product was composed of 26% by weight of the EPEL, 2% by weight of p-isomer of the EPEL, 49% by weight of the unreacted EPEA, 4% by weight of p-isomer of the EPEA and 19% by weight of unidentified substances. That is, it is fair to say that the thus treated fraction could contain a high proportion of the dehydrogenation product EPEL. This fraction was then employed in the oxidizing reaction without being purified.

In addition, the EPEL contained in the dehydrogenated fraction was compared with the EPEL which had been synthesized separately, with respect to analytical results by the use of GC, IR and the like.

Synthesis of 1,1-(3-ethylphenyl)phenylethanol

In a 2 liter flask equipped with a reflux condenser and a stirrer, 50 ml of ether which had been dried with metallic sodium and 28 g (1.15 mols) of metallic magnesium were placed. While stirring the resultant mixture at room temperature, 500 ml of a dry ether solution containing 160 g (1.02 mols) of benzene bromide was gradually added dropwise to the resultant mixture over 2 hours. The reaction temperature was maintained at 35° C. After the completion of the dripping addition, stirring was further continued at 35° C. for 1 hour. Next, 500 ml of a dry ether solution containing 148 g (1.00 mol) of m-ethylacetophenone was gradually added thereto dropwise over 2 hours, and stirring was further carried out at 35° C. for 1 hour. After the resultant reaction solution had been thrown into an ice water, the separation of solutions was made to recover an ether layer, and the latter was then distilled off under a reduced pressure in order to obtain 1,1-(3-ethylphenyl)-phenylethanol having the formula. This alcohol could be fed to a subsequent process directly without any additional purification, because of dehydrating relatively easily by heating or the like.

Synthesis of 1,1-(3-ethylphenyl)phenylethylene

In a 500 ml three-necked flask equipped with a dropping funnel, 20 g of potassium hydrogensulfate was placed, and was then heated up to 230° to 240° C. under a reduced pressure. Afterward, the alcohol prepared in the preceding paragraph was added thereto dropwise through the dropping funnel. In consequence, the alcohol was dehydrated to an olefin, which was immediately distilled off and was recovered in an outside receiver. From the thus recovered product, water was separated, and vacuum distillation was further carried out in order to form 150 g of the EPEL in a yield of 72%. The analytical results of the product are as follows:

Boiling point: 172° to 174° C./3 mmHg
IR (Neat)cm$^{-1}$: 3060, 3040, 2960, 1600, 1490, 890, 800, 770, 700
$^1$H-NMR (CCl$_4$, δppm): 6.80 to 7.60 (9H, multiplet); 5.35 (2H, singlet); 2.40 to 2.85 (2H, quartet); 1.05 to 1.40 (3H, triplet);
Elemental analysis (as C$_{16}$H$_{16}$):
Calculated values: C=92.31%, H=7.69%.
Found values: C=92.33%, H=7.67%.

Experiment 2

In a reactor equipped with a stirrer, benzene was brought into contact with ethylene in a molar ratio of benzene:ethylene being 9:1 in the presence of aluminum chloride at a temperature of 130° C. at a pressure of 4.9 kg/cm$^2$ for 1 hour in a liquid phase in order to convert all of ethylene. An amount of used aluminum chloride was 0.0034 part by weight based on ethylbenzene produced. Aluminum chloride was then removed from the resultant alkylated product, and analysis was carried out by means of GC. It was found from the analytical results that there existed therein 49.0% by weight of benzene, 32.9% by weight of ethylbenzene, 17.5% by weight of polyethylbenzenes and 0.5% by weight of heavier substances. The alkylated product was then distilled to recover benzene, ethylbenzene and polyethylbenzenes, so that heavier substances were obtained in an amount of 0.014 part by weight based on ethylbenzene produced. These heavier substances were further subjected to distillation in order to procure a fraction having a boiling point of 290° to 305° C. (in terms of atmospheric pressure), and the procured fraction was then analyzed by means of GC. It was found from the analytical results that the fraction was composed of 82% by weight of the EPEA and the remainder consisting of polyalkylbenzenes and various other hydrocarbons.

The above mentioned distillation was carried out at a reduced pressure of 5 mmHg, the number of theoretical separation plates being 15.

An iron oxide series dehydrogenating catalyst (trade name 64C; Nissan Girdler Co., Ltd.) containing chromium oxide and alumina was prepared so as to have a grain diameter of 0.5 to 1 mm, and a stainless pipe having an inner diameter of 10 mm and a length of 60 cm was then filled with the thus prepared dehydrogenating catalyst. The above mentioned fraction was caused to pass through the catalytic layer at 40 ml/hr together with water at 40 ml/hr at a temperature of 400° C. under atmospheric pressure via a preheating pipe in order to accomplish dehydrogenation therein. The reaction product was then cooled to room temperature, followed by a gas-liquid separation. The resultant organic layer was afterward subjected to the GC analysis with the intention of making sure of reactivity and selectivity. The analytical results indicated that the reaction product was composed of 28% by weight of the EPEL, 53% by weight of the unreacted EPEA and 19% by weight of unidentified substances. That is, it is fair to say that the thus treated fraction could contain a high proportion of the dehydrogenation product EPEL. This fraction was then employed in the oxidizing reaction without being purified.

Experiments 3 to 6

A dehydrogenation reaction was carried out in the same manner as in Experiment 2 with the exception that temperatures of dehydrogenation and amounts of water to be fed were changed. The results are set forth in Table 1.

TABLE 1

| Experiment No. | Reaction Temperature (°C.) | Amount of Water (ml/hr) | Composition of Products (wt %) | | |
|---|---|---|---|---|---|
| | | | EPEL | EPEA | Unknown |
| 3 | 350 | 40 | 14 | 66 | 20 |
| 4 | 450 | 40 | 32 | 38 | 30 |
| 5 | 450 | 80 | 35 | 36 | 29 |
| 6 | 500 | 40 | 40 | 21 | 39 |

Experiment 7

In a 200 ml reactor equipped with a stirrer, 72 g of the fraction containing the EPEL prepared in Experiment 1 and 0.04 g of cobalt naphthenate were placed, and a reaction temperature was set to 100° C. and pure oxygen was then blown thereinto at a feed rate of 100 ml/min at atmospheric pressure for 10 hours. The reaction product was afterward cooled to room temperature, and the used catalyst was then removed therefrom. Next, analysis was carried out with the aid of GC, and the results were indicative of the fact that the conversion of the EPEL was 97% and the selectivity of the EPEL into the EBP was 89%. This reaction mixture was then distilled to thereby obtain 14 g of the fraction of 320° to 333° C. (in terms of atmospheric pressure). As a result of the analysis by the use of GC, the purity of the EBP was 95%. It is to be noted that ortho- and para-isomers which were position isomers of the EBP were scarcely contained therein.

Experiment 8

The procedure of Experiment 7 was repeated with the exception that 0.04 g of iron naphthenate was used in place of cobalt naphthenate. In this case, the conversion of the EPEL was 86% and the selectivity of the EPEL into the EBP was 87%.

Experiment 9

The procedure of Experiment 7 was repeated with the exception that air was substituted for pure oxygen at 200 ml/min. In this case, the conversion of the EPEL was 72% and the selectivity of the EPEL into the EBP was 83%.

Experiment 10

In a 500 ml reactor equipped with a stirrer, 72 g of the fraction containing the EPEL prepared in Experiment 1, 12.8 g of potassium permanganate and 120 m of water were placed, and a reaction was performed at a reaction temperature of 30° C. for 20 hours. Into the resultant reaction mixture, 120 ml of benzene was poured for extraction, and after the separation of a benzene layer, benzene was distilled away. As a result of the analysis of the resultant oily substance by the use of GC, it was found that the conversion of the EPEL was 35% and the selectivity of the EBP was 73%. This oily substance was then distilled to obtain 4.5 g of a fraction of 320° to 333° C. (in terms of atmospheric pressure). As a result of the GC analysis, it was found that the purity of the EBP was 90%. Further, it is to be noted that ortho- and para-isomers which were position isomers of the EBP were scarcely contained therein.

Experiment 11

By employing the fraction containing the EBP obtained in Experiment 7, a ketoprofen was synthesized in accordance with the above mentioned Spanish patent.

Synthesis of 3-(1-bromoethyl)benzophenone

Into a 200 ml reactor equipped with a reflux condenser and a stirrer, 60 ml of carbon tetrachloride and 10 g of the EBP distillate obtained in Experiment 7 were introduced. While stirring the resultant mixture at room temperature, 8.6 g of N-bromosuccinimide and 0.14 g of benzoyl peroxide were added thereto, and reflux was perfomed for 8 hours while stirring the reaction solution. After the reaction solution had been cooled to room temperature, the succinimide was filtered out, and carbon tetrachloride was distilled off from a filtrate under a reduced pressure. The spectrum data of the obtained product were in accord with those of 3-(1-bromoethyl)benzophenone.

Synthesis of 3-(1-hydroxyethyl)benzophenone

In an autoclave, 100 ml of water and 3.3 g of calcium carbonate and 10 g of 3-(1-bromoethyl)benzophenone were placed, and were then heated at 120° C. for 6 hours. The resultant reaction solution was extracted with benzene, and a formed benzene layer was then dried with anhydrous sodium sulfate, followed by distilling off the solvent. The resultant product had the spectrum data which were identical with those of 3-(1-hydroxyethyl)benzophenone.

Synthesis of Ketoprofen

In 50 ml of anhydrous ethanol containing 1.5% of hydrogen chloride, 10 g of 3-(1-hydroxyethyl)benzophenone was dissolved, and an anhydrous ethanol solution containing 0.1 g of $[P(CH_3)_3]PdCl_2$ was then added thereto. This solution was introduced into an autoclave and was then heated at 95° C. at 500 atms for 5 hours in an atmosphere of carbon monoxide. The reaction solution was then transferred to a 200 ml reactor equipped with a reflux condenser and a stirrer, and 5 ml of concentrated hydrochloric acid was added thereto. Afterward, reflux was carried out for 4 hours in a nitrogen atmosphere. Water was then added to the reaction solution, and extraction was performed by the use of ether. The resultant ether layer was washed with water and was then extracted with a 5% aqueous potassium hydroxide solution. After a water layer had been acidified with hydrochloric acid, extraction was performed by the utilization of ether again. The ether layer was then washed with water and dried with anhydrous sodium sulfate, and ether was distilled off under a reduced pressure. The desired α-(3-benzoylphenyl)propionic acid [Ketoprofen (trade name)] was obtained by its recrystallization from benzene/petroleum ether. Spectra and a melting point of the thus obtained Ketoprofen were the same as those of its authentic sample.

Experiment 12

The fraction containing the EPEL obtained in Experiment 1 was oxidized in the same manner as in Experiment 7 with the exception that each of manganese naphthenate, chromium naphthenate and nickel naphthenate was substituted for cobalt naphthenate as an oxidizing catalyst. The results are as follows:

| Catalyst | Conversion[1] | Selectivity[2] |
|---|---|---|
| Manganese naphthenate | 95% | 90% |
| Chromium naphthenate | 96% | 91% |
| Nickel naphthenate | 94% | 88% |

[1]Conversion of EPEL
[2]Selectivity of EPEL into EBP

In all the cases, the fractions of 320° to 333° C. (in terms of atmospheric pressure) had about the same purity of the EBP obtained in Experiment 7.

Experiment 13

The fraction containing the EPEL obtained in Experiment 1 was oxidized in the same manner as in Experiment 7 with the exception that the oxidation was carried out in the absence of any catalyst at the oxidizing temperature of 120° C.

The conversion of the EPEL and the selectivity of the EPEL into the EBP were 96% and 88%, respectively.

In this case, the fraction of 320° to 333° C. (in terms of atmospheric pressure) had about the same purity of the EBP as the purity of the EBP obtained in Experiment 7.

What is claimed is:

1. A method for preparing 3-ethylbenzophenone in a high purity which consists essentially of the steps of alkylating benzene with ethylene in the presence of an alkylating catalyst comprising aluminum chloride at a temperature within the range of about 0° to 175° C. to obtain an alkylated product composed mainly of unreacted benzene, ethylbenzene, polyethylbenzene and heavier substances; subjecting said alkylated product to distillation in order to recover therefrom a fraction which has a temperature range of boiling points within the range of 275° to 310° C. (in terms of atmospheric pressure); dehydrogenating said recovered fraction at a reaction temperature within the range of 200° to 700° C. in the presence of a dehydrogenation catalyst comprising an iron oxide; oxidizing said dehydrogenated fraction in a liquid phase with molecular oxygen at a temperature of 30° to 250° C.; and performing a distillation to recover therefrom 3-ethylbenzophenone represented by the formula (I):

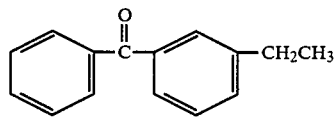

(I)

2. A method for preparing 3-ethylbenzophenone according to claim 1 wherein said oxidizing is conducted in the presence of an oxidizing catalyst selected from Groups IV-b, VII-b and VIII of the periodic table.

3. A method for preparing 3-ethylbenzophenone according to claim 2 wherein said oxidizing catalyst is selected from naphthenates of chromium, manganese, tungsten, molybdenum, platinum, palladium, cobalt, nickel, iron, rhodium and ruthenium.

4. A method according to claim 1 wherein said distillation to recover therefrom 3-ethylbenzophenone is carried out at a temperature within the range of 310° to 340° C. (in terms of atmospheric pressure).

5. A method according to claim 4 wherein said distillation is carried out at a temperature within the range of 320° to 333° C. (in terms of atmospheric pressure).

6. A method according to claim 2 wherein said distillation to recover therefrom 3-ethylbenzophenone is carried out at a temperature within the range of 310° to 340° C.

7. A method according to claim 6 wherein said distillation is carried out at a temperature within the range of 320° to 333° C. (in terms of atmospheric pressure).

8. A method for preparing 3-ethylbenzophenone in a high purity which consists essentially of the steps of alkylating benzene with ethylene in the presence of an alkylating catalyst comprising aluminum chloride at a temperature within the range of about 0° to 175° C. to obtain an alkylated product composed mainly of unreacted benzene, ethylbenzene, polyethylbenzene and heavier substance; subjecting said alkylated product to distillation in order to recover therefrom a fraction which has a temperature range of boiling points within the range of 275° to 310° C. (in terms of atmospheric pressure); dehydrogenating said recovered fraction at a reaction temperature within the range of 200° to 700° C. in the presence of dehydrogenation catalyst comprising an iron oxide; oxidizing said dehydrogenated fraction in a liquid phase with an oxidizing agent comprising a peroxide at a reaction temperature of 0° to 100° C. in an inert solvent; and performing distillation to recover therefrom 3-ethylbenzophenone represented by the formula (I):

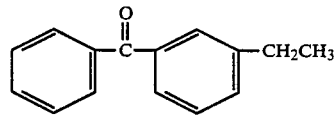

(I)

9. A method for preparing 3-ethylbenzophenone according to claim 8 wherein said peroxide is selected from a permanganate, a chromate, lead tetraacetate, a periodate, ruthenium tetroxide, osumium tetroxide, hydrogen peroxide and ozone.

10. A method according to claim 8 wherein said distillation to recover therefrom 3-ethylbenzophenone is carried out at a temperature within the range of 310° to 340° C. (in terms of atmospheric pressure).

11. A method according to claim 10 wherein said distillation is carried out at a temperature within the range of 320° to 333° C. (in terms of atmospheric pressure).

* * * * *